United States Patent
Monicke et al.

(10) Patent No.: US 12,004,970 B2
(45) Date of Patent: Jun. 11, 2024

(54) ORTHOPEDIC COMPONENT HAVING AT LEAST TWO STRUCTURAL PARTS CONNECTED BY AN ORIENTING DEVICE AND ADHESIVE

(71) Applicant: OTTOBOCK SE & CO. KGAA, Duderstadt (DE)

(72) Inventors: Carsten Monicke, Duderstadt (DE); Darshan Rane, Millcreek, UT (US); Anthony Lee Stephenson, North Salt Lake, UT (US)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 10 days.

(21) Appl. No.: 16/952,335

(22) Filed: Nov. 19, 2020

(65) Prior Publication Data

US 2021/0186712 A1 Jun. 24, 2021

Related U.S. Application Data

(60) Continuation of application No. 16/836,566, filed on Mar. 31, 2020, now Pat. No. 11,590,005, which is a
(Continued)

(30) Foreign Application Priority Data

May 7, 2014 (DE) .......................... 102014006570.7

(51) Int. Cl.
*A61F 2/66* (2006.01)
*A43B 7/1405* (2022.01)
(Continued)

(52) U.S. Cl.
CPC ............ *A61F 2/5046* (2013.01); *A43B 7/141* (2013.01); *A61F 2/66* (2013.01); *B29C 65/54* (2013.01);
(Continued)

(58) Field of Classification Search
CPC ............ A61F 2/60; A61F 2/66; A61F 2/6607
See application file for complete search history.

(56) References Cited

U.S. PATENT DOCUMENTS

| 3,510,968 A | 5/1970 | Hobbs, Jr. et al. |
| 3,812,604 A | 5/1974 | Sato |

(Continued)

FOREIGN PATENT DOCUMENTS

| CN | 1395479 A | 2/2003 |
| DE | 1884675 U | 12/1963 |

(Continued)

OTHER PUBLICATIONS

PCT International Search Report for PCT International Patent Application No. PCT/EP2015/000917, dated Aug. 5, 2015.

*Primary Examiner* — Marcia L Watkins
(74) *Attorney, Agent, or Firm* — HOLLAND & HART LLP

(57) ABSTRACT

A method for connecting at least two structural parts of an orthopedic component, wherein the structural parts are retained in an orienting device while oriented in relation to each other, and an intermediate space thus being formed between the structural parts. The orienting device and the structural parts together form a cavity, which has a flow connection to at least one feed connection, via which an adhesive for adhesively bonding the structural parts is introduced into the cavity.

12 Claims, 14 Drawing Sheets

Related U.S. Application Data division of application No. 15/305,643, filed as application No. PCT/EP2015/000917 on May 5, 2015, now abandoned.

(51) Int. Cl.

| | | |
|---|---|---|
| *A61F 2/50* | (2006.01) | |
| *B29C 65/00* | (2006.01) | |
| *B29C 65/54* | (2006.01) | |
| *B29C 65/78* | (2006.01) | |
| *B29C 65/48* | (2006.01) | |
| *B29K 105/06* | (2006.01) | |
| *B29L 31/00* | (2006.01) | |
| *B29L 31/50* | (2006.01) | |

(52) U.S. Cl.
CPC ...... *B29C 65/7826* (2013.01); *B29C 66/1222* (2013.01); *B29C 66/1226* (2013.01); *B29C 66/301* (2013.01); *B29C 66/543* (2013.01); *B29C 66/721* (2013.01); *B29C 66/742* (2013.01); *B29C 66/8223* (2013.01); *B29C 66/828* (2013.01); *B29C 66/845* (2013.01); *A61F 2002/6614* (2013.01); *A61F 2002/6657* (2013.01); *B29C 65/4815* (2013.01); *B29C 65/483* (2013.01); *B29C 65/542* (2013.01); *B29C 66/8322* (2013.01); *B29K 2105/06* (2013.01); *B29L 2031/504* (2013.01); *B29L 2031/7532* (2013.01)

(56) References Cited

U.S. PATENT DOCUMENTS

| | | | |
|---|---|---|---|
| 4,892,553 | A | 1/1990 | Prahl |
| 4,959,073 | A | 9/1990 | Merlette |
| 5,156,631 | A | 10/1992 | Merlette |
| 5,171,276 | A | 12/1992 | Caspari et al. |
| 5,310,221 | A | 5/1994 | Schmidt |
| 6,669,737 | B2 | 12/2003 | Mosler et al. |
| 7,824,446 | B2 | 11/2010 | Christensen et al. |
| 8,540,781 | B2 | 9/2013 | Nissels et al. |
| 2004/0068327 | A1 | 4/2004 | Christensen |
| 2005/0033450 | A1 | 2/2005 | Christensen |
| 2012/0179274 | A1 | 7/2012 | Christensen |
| 2012/0199274 | A1 | 7/2012 | Christensen |
| 2013/0144403 | A1 | 6/2013 | Lecomte et al. |
| 2013/0173023 | A1 | 7/2013 | Lecomte et al. |
| 2014/0039642 | A1 | 2/2014 | Nijiman et al. |
| 2014/0046456 | A1 | 2/2014 | Smith et al. |
| 2015/0289996 | A1* | 10/2015 | Smith ............... A61F 2/66 623/53 |
| 2017/0049584 | A1 | 2/2017 | Pusch et al. |

FOREIGN PATENT DOCUMENTS

| | | |
|---|---|---|
| DE | 155950 A1 | 7/1970 |
| DE | 2906752 A1 | 3/1980 |
| DE | 3935129 A1 | 5/1990 |
| DE | 10305382 A1 | 8/2003 |
| EP | 0043874 A1 | 1/1982 |
| GB | 2034857 A | 6/1980 |
| RU | 2102940 C1 | 1/1998 |
| RU | 2122381 C1 | 11/1998 |

* cited by examiner

ORTHOPEDIC COMPONENT HAVING AT LEAST TWO STRUCTURAL PARTS CONNECTED BY AN ORIENTING DEVICE AND ADHESIVE

CROSS REFERENCE TO RELATED APPLICATIONS

This application is a Continuation of U.S. patent Ser. No. 11,590,005, filed 31 Mar. 2020, which is a Divisional of U.S. patent application Ser. No. 15/305,643, filed 20 Oct. 2016, which is a National Stage Entry of PCT International Patent Application No. PCT/EP2015/000917, filed 5 May 2015, and entitled "METHOD FOR CONNECTING AT LEAST TWO STRUCTURAL PARTS OF AN ORTHOPEDIC COMPONENT AND ORTHOPEDIC COMPONENT HAVING AT LEAST TWO STRUCTURAL PARTS," which claims priority to Germany Patent Application No. 102014006570.7 filed 7 May 2014, the entire disclosures of which are incorporated herein by this reference.

TECHNICAL FIELD

The invention relates to a method for connecting at least two structural parts of an orthopedic component, in which the structural parts are retained in an orienting device while oriented in relation to each other with an intermediate space thus being formed between the structural parts. The invention also relates to an orthopedic component having at least two structural parts which are adhesively bonded to one another at a distance from one another.

BACKGROUND

Structural parts, in particular those formed from prefabricated semifinished products based on fiber-reinforced plastics, can be connected to one another in various ways. Besides a screwed connection, in which case through-holes are formed or made through both structural parts, through which holes threaded bolts are fitted and connected to one another, it is also possible for the two structural parts to be adhesively bonded to one another. For this purpose, the parts are oriented in relation to one another, are held in relation to one another in the oriented form, and an intermediate space is formed between the structural parts, which space is filled with an adhesive. The assignment of the two parts is maintained for as long as it takes for the adhesive to become sufficiently cured. The retaining devices provided as appropriate are then removed and the adhesive that routinely escapes via the joint area is removed within the scope of a finishing operation. This finishing operation is laborious and can only be carried out by means of time-consuming, manual work.

SUMMARY

The object of the present invention is to provide a method for connecting at least two structural parts of an orthopedic component and also an orthopedic component as such, which can be realized more economically, ensure a precise orientation of the structural parts in relation to one another, and reduce the finishing effort.

This object is achieved in accordance with the invention by a method having the features disclosed herein and by an orthopedic component having the features disclosed herein. Advantageous embodiments and developments of the invention are also disclosed in the description, and in the drawings.

This object is achieved in accordance with the invention by a method having the features of the main claim and by an orthopedic component having the features of the additional independent claim. Advantageous embodiments and developments of the invention are disclosed in the dependent claims, in the description, and in the drawings.

The method for connecting at least two structural parts of an orthopedic component, in which the structural parts are retained in an orienting device while oriented in relation to each other with an intermediate space thus being formed between the structural parts, makes provision for the orienting device and the structural parts to together form a hollow space, which is fluidically connected to at least one feed connection and via which an adhesive for adhesively bonding the structural parts is introduced into the hollow space. Due to the orienting device, which is formed as what is known as a molding shell and remains on the structural part, it is possible, besides an orientation of the structural parts in relation to one another, to also form a hollow space, which is substantially closed and generally has just one feed connection, for example a drilled hole in a side wall, through which adhesive is introduced into the hollow space. The hollow space is delimited at least in part by the structural parts so that the introduced adhesive comes into contact with the structural parts and can adhesively bond these to one another. The hollow space preferably also has an outlet channel so that, when the adhesive is introduced into the hollow space, the air can be displaced so that the hollow space can be completely filled. As soon as adhesive escapes from the outlet channel, it is ensured that the hollow space has been completely filled with adhesive, and the filling with adhesive is finished, the feed connection and outlet channel are closed, and the adhesive is left to cure. In this way, on the one hand the assignment of the structural parts to one another is produced in a reproducible and precise manner in relation to one another and on the other hand adhesive is prevented from coming into contact with the structural parts outside the hollow space, whereby finishing operations are avoided. The adhesive in the cured state preferably has resilient properties, for example in the case of a foot prosthesis so as not to tear or fracture as the prosthetic foot rolls from heel to toe. PU, TPU and/or TPE are preferably used as adhesives. For rigid connections in areas that are exposed to a smaller or non-critical dynamic load, resins can also be used, which in particular is advantageous in the case of fiber-reinforced material, since the same resins used to form the matrix of the fibers can be used, thus resulting in a good connection between the structural parts and the adhesive.

The structural parts are retained oriented in relation to one another until the adhesive has cured. This can be achieved for example in that receptacles, slots and guides are arranged or formed in the orienting device so that the orienting device is automatically secured to the structural parts. Alternatively, it is possible for the structural parts to be fixed to the orienting device via a clamping device or another fixing device, for example by means of a clamp, so that, even when the adhesive is fed under pressure, the orientation of the structural parts in relation to one another is not cancelled. In a particular embodiment, an additional orientation of the structural parts in a plane can also be provided via an apparatus or an auxiliary device. Whereas the orienting device ensures the position of the structural parts in a plane and for example at one end of the orthopedic component, the auxiliary device or apparatus can ensure the orientation in another plane or orientation, so that the orienting device does not on its own position the structural parts in relation to one another. The auxiliary device ensures the orientation in another plane or orientation, and by way of example an edge can be spared and the orientation and positioning of the free ends of the structural parts can be implemented via the auxiliary device, for example the press or a clamping device.

At least one structural part is advantageously embedded in the adhesive, wherein there is no need for complete embedment in the adhesive, rather it is sufficient when at least one structural part comes into contact with the adhesive at more than one surface, for example on an upper side and a lower side or on a number of side faces, in order to provide an adhesive bonding of the structural part on a number of sides. In principle, it is sufficient when just one surface of the structural part in question, for example an upper side, side face or lower side of a leaf spring-like or rib-like part is connected to the adhesive in order to provide an adhesive bond to the other structural part and the orienting device.

A development of the invention makes provision for at least one structural part to be pressed during the adhesive bonding against the orienting device, whereby it is not necessary to design the orienting device as an independently sealing mold part assigning the structural parts to one another. It is thus sufficient for a region above a first structural part, which region rests on the surface of the first structural part and is upwardly open, to be surrounded via spacers and a peripheral edge. This upwardly open receptacle, which for example can have guide edges for the second structural part, is closed by the second structural part in that the second structural part is placed against the orienting device and is acted on by a force in the direction of the first structural part.

The hollow space is sealed by holding the structural parts, naturally inclusive of the feed connection and the outlet channel, so that a substantially closed hollow space is produced, from which the fed adhesive can escape only through the outlet channel. Due to the practically complete sealing of the hollow space or the hollow spaces, it is possible to avoid finishing operations or to reduce these to a minimum.

The adhesive can be introduced into the hollow space via feed devices, for example feed tubes, wherein the feed devices and where applicable also outlet devices such as outlet tubes remain on the orienting device until the adhesive is cured and are removed once the adhesive has cured. The feed devices and where applicable outlet devices such as tubes, pipes and the like can be formed as separate components which are inserted into the relevant channels and prevent adhesive from coming into contact with the surface both of the structural parts and of the orienting device as said adhesive cures. By removing the feed devices and the outlet devices, it is possible to produce a cleaner connection without finishing operations and without the risk of adhesive residues on the respective components.

The orthopedic component having at least two structural parts which are adhesively bonded to one another at a distance from one another makes provision for the structural parts to be retained in an orienting device while oriented in relation to one another and for the orienting device to have at least one spacer, which distances the structural elements from one another. Due to the one or more spacers, it is possible to form a hollow space between the structural parts which is filled by the adhesive, advantageously completely, so that an adhesive bonding of the structural parts to one another over the greatest area possible is ensured.

The orienting device is adhesively bonded to the structural parts and remains on the structural parts after the adhesive bonding so that the orienting device is part of the orthopedic component. The orienting device thus serves on the one hand as a mold and on the other hand as a functional component, for example for protection, and therefore the orienting device can be referred to as a molding shell, which on the one hand constitutes a lost mold and on the other hand performs an additional function, specifically the protection of the structural parts by means of an appropriate material selection and/or as a rolling contour due to its shaping on the lower side. The orienting device is advantageously produced from a flexible, resilient plastic, which surrounds the structural elements at least in part so that functional requirements which cannot be satisfied by the structural parts per se, for example on account of the material characteristics, are also satisfied by the orienting device. By way of example, it is possible that the orienting device has a cushioning function and a profiling function so that a shaping of the structural parts can additionally be perceived through the orienting device.

The orienting device has at least one insertion opening for at least one structural element, wherein the shape of the insertion opening corresponds substantially to the contour of the structural part. The insertion opening enables the assignment of the structural part to the orienting device when the orienting device is fitted onto the structural element or the structural element is inserted into the orienting device. Guide elements or devices are provided within the orienting device, for example slots, grooves or protrusions, so that the orienting device is secured to the structural part in a defined manner. The insertion opening itself bears as closely as possible against the contour of the structural part in order to avoid an undesirable escape of adhesive as the hollow space is filled with adhesive.

The structural parts are advantageously formed as leaf springs, which are arranged parallel to one another and come into contact with the adhesive in the region of the hollow space so that a stable and large-area adhesive bonding of the leaf springs to one another is present there.

At least one structural part is preferably surrounded on a number of sides by the adhesive in order to ensure the most defined and stable adhesively bonded connection possible between the structural parts and the orienting device.

At least one connection channel is advantageously formed in the orienting device, which channel connects two hollow spaces separated by a structural part to one another. It may thus be possible for a hollow space to be formed on the lower side of the structural part, which hollow space is formed between the structural part and the orienting device. Due to this lower hollow space, the adhesive by way of example can be introduced so that it is necessary to convey the adhesive from the lower-side hollow space into the hollow space formed between the structural parts. From there, a connection channel can lead on to either the outlet channel, which is arranged at the advantageously geodetically upper or highest point in order to expel the air completely from the hollow spaces when the adhesive is introduced. It is also possible for more than two structural parts to be adhesively bonded in a manner oriented in relation to one another, such that a hollow space is provided between each two structural parts, i.e. in the case of three structural parts at least two hollow spaces are thus provided, which have to be connected to one another in order to avoid having to provide a number of feed connections in order to fill the hollow space or the hollow spaces. In principle, it is also possible, in the case of a number of hollow spaces separated from one another, to provide each hollow space or a number of hollow spaces with a feed connection and a corresponding outlet channel.

The orthopedic component can be formed as a prosthetic foot or orthotic component.

The orienting device can bear against or surround at least one structural part at least on three sides. With a planar embodiment of the structural part and a placement and laying in a frame, the frame is generally arranged on the front side and the two lateral edges of the structural part. If a structural part is inserted into a slot, the orienting device bears at least in part against the lower side, the upper side, the front side, and the two side faces and protrudes out from the insertion opening.

The structural part is preferably formed as a fiber-reinforced plastics part, however it is also possible in principle to adhesively bond other structural parts to one another and to fix these to one another together with the orienting device via an adhesive connection of this type. It is also possible for structural parts made of different materials, for example metals and fiber composite materials, to be adhesively bonded to one another via a device of this type, since there is no need for direct contact between the structural parts and the distanced assignment of the structural parts with intermediate positioning of the adhesive ensures a distanced fastening of the structural parts to one another. In addition, a protective sheathing, at least a partial protective sheathing, is provided via the orienting device.

BRIEF DESCRIPTION OF THE DRAWINGS

Exemplary embodiments of the invention will be explained in greater detail hereinafter on the basis of the accompanying drawings, in which.

DETAILED DESCRIPTION

Figure 1:
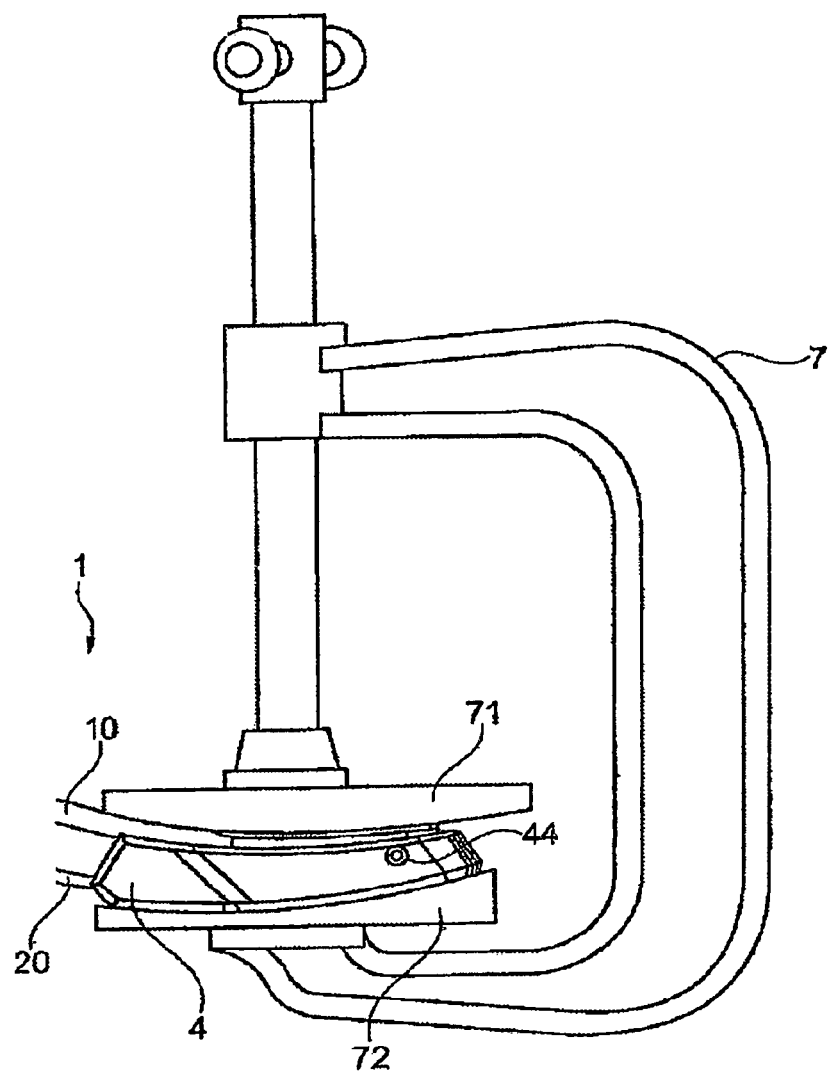
FIG. 1 shows a side view of an orthopedic component during manufacture.

FIG. 1, in a side view, shows a schematic illustration of a front part of an orthopedic component 1, which is formed as a prosthetic foot. The prosthetic foot has two structural parts 10, 20, which are produced as leaf springs made of a fiber-reinforced plastic. The forefoot region of the orthopedic component 1 is illustrated: the first structural part 10 is a forefoot spring and the second structural part 20 is a base spring. The forefoot spring 10 extends upwardly at an incline to an upper connection point, at which fastening devices or connection means for fastening can be fastened to a lower leg rod or a lower leg shaft. The base spring 20 leads into the heel region, wherein a heel spring can extend from the base spring 20 to the forefoot spring 10 and/or the upper connection means.

The structural parts 10, 20 are assigned to an orienting device 4, which is formed as a plastic injection-molded part. The orienting device 4 can consist of a polyurethane, an engineering polyethylene, an engineering polyurethane, rubber, or another plastic, preferably elastomer. The orienting device 4 has an insertion slot for the second structural part 20 and a receiving region on the upper side for the first structural part 10, against which region the first structural part 10 can be placed. The support region is bordered by walls so that the first structural part 10 can be placed in a defined position in relation to the orienting device 4 when the contour of the structural part 10 bears against the walls around the support region.

The second structural part 20 is inserted into a slot (not illustrated) within the orienting device so that the lower side of the second structural part 20 or of the leaf spring is covered by a closed surface of the lower side of the orienting device 4. A spacer is formed between the two structural parts 10, 20 and holds the two structural parts 10, 20 at a distance from one another. Due to the insertion of the second structural part 20 into the orienting device 4, this structural part 20 is also assigned in a defined manner, for example in that the second structural part 20 is guided in a slot or in a groove within the receiving device 4. The two structural parts 10, 20 and the receiving device 4 thus form a hollow space, which is substantially closed. A feed connection 44 is provided in a side wall of the orienting device 4, which feed connection is fluidically connected to the hollow space (not illustrated) and through which adhesive can be introduced or pumped into the hollow space. An outlet channel is provided on the side facing away from the feed connection 44, which outlet channel is likewise fluidically connected to the hollow space so that the air located within the hollow space can escape and the hollow space can be completely filled with adhesive.

The structural parts 10, 20 and the orienting device 4 are held in a press 7, which can be formed as a conventional vice. Two press shoes 71, 72 are arranged on the press 7 and have a contour corresponding to the assigned contour of the orthopedic component 1. In the illustrated exemplary embodiment the upper press shoe 71 is provided with a convex curvature and the lower press shoe 72 is provided with a concave curvature so that on the one hand the lower side of the receiving device 4 and on the other hand the upper side of the first structural part 10 can bear over the entire surface against the surface of the relevant press shoes 71, 72. If the press 7 is closed and pressure is exerted onto the press shoe 71, 72, the first structural part 10 will be pressed against the surface of the support face on the orienting device 4 so that the hollow space formed between the structural parts 10, 20 above and below and at the side faces by means of the orienting device 4 is closed and adhesive can be fed only through the feed connection 44, and air and any excess adhesive can escape through the outlet channel.

Following the introduction of the adhesive, the pressing force is maintained until the adhesive has cured, so that a permanent connection between the first structural part 10, the second structural part 20, and the orienting device 4 is attained. After curing of the adhesive, the orienting device 4 remains on the orthopedic component 1 and serves in turn as protection for the structural parts 10, 20 and on the other hand as functional component of the orthopedic component, for example as a shaping for the prosthetic foot, as a cushion, as a sole structure, or in other embodiments as a receiving device or protective device for further components.

Figure 2:
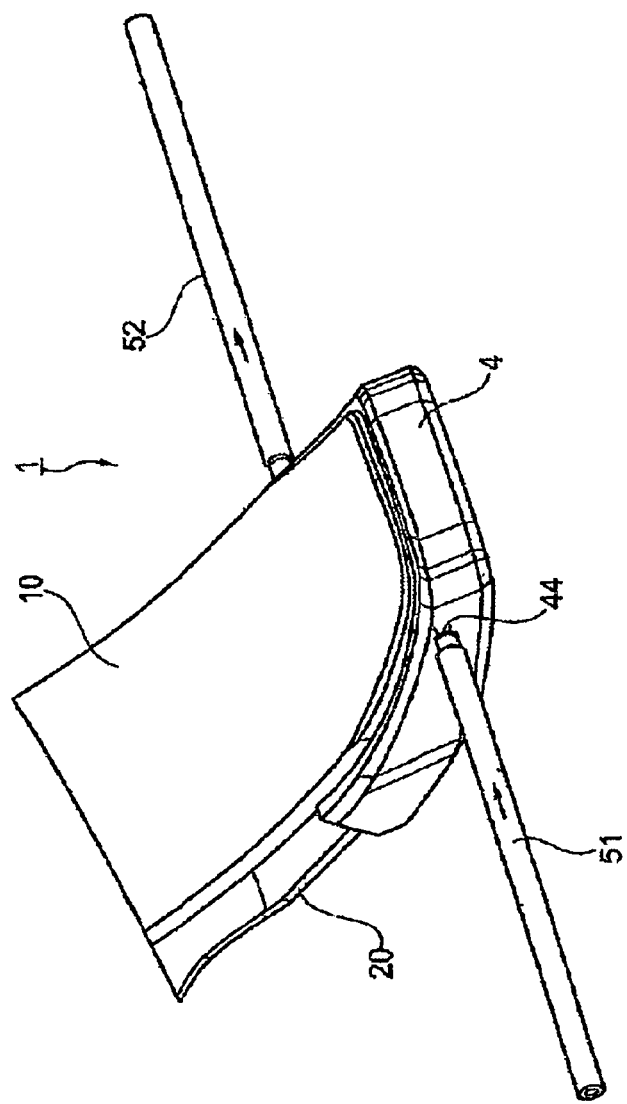
FIG. 2 shows a perspective view with feed and outlet devices.

FIG. 2, in a perspective oblique plan view, shows the manufacture of the orthopedic component 1, or at least the connection of the structural parts 10, 20 to the orienting device 4. A feed device 51 is attached to the orienting device 4 at the feed connection 44, which feed device in the illustrated exemplary embodiment is formed as a tube or pipe and through which adhesive is introduced into the hollow space (not illustrated) as indicated by the arrow. The hollow space is formed and closed on the upper side and on the lower side by the structural parts 10, 20, on the front side and on the side edges by the side walls of the orienting device 4, and on the rear side between the structural parts 10, 20 by a spacer, which bears tightly both against the lower side of the first structural part 10 and against the upper side of the second structural part 20. In FIG. 2 the press 7 is not illustrated, however the assignment of the respective components 4, 10, 20 by the press 7 or another suitable fixing device is maintained during the feed of the adhesive.

Adhesive is introduced into the hollow space through the feed device 51 and the feed connection 44, and the air disposed in the hollow space is displaced by the adhesive and is transported away by an outlet device 52. The outlet device 52 is connected at an outlet channel (not illustrated), which is fluidically connected to the hollow space within the receiving device 4, so that air and any excess adhesive can escape from the outlet channel through the outlet opening 51, as indicated by the arrow. Both the feed connection 44 and the outlet channel are preferably arranged in a spacer, which ensures that the structural parts 10, 20 are held at a distance from one another. It is thus ensured that the feed connection 44 and the outlet channel are blocked by the arrangement of the structural parts 10, 20 on or in the orienting device 4.

The press 7 (not illustrated) holds the assignment of the components 4, 10, 20 in relation to one another until the adhesive has cured. Once the adhesive has cured, the feed device 51 and the outlet device 52 are separated from the orienting device 4, for example snapped off, so that a practically smooth termination of the orienting device 4 in the region of the feed connection 44 and the outlet channel can be achieved. This can be ensured for example by a predetermined breaking point on the feed device 51 and/or the outlet device 52 in the region of the connection to the orienting device 4.

Figure 3:
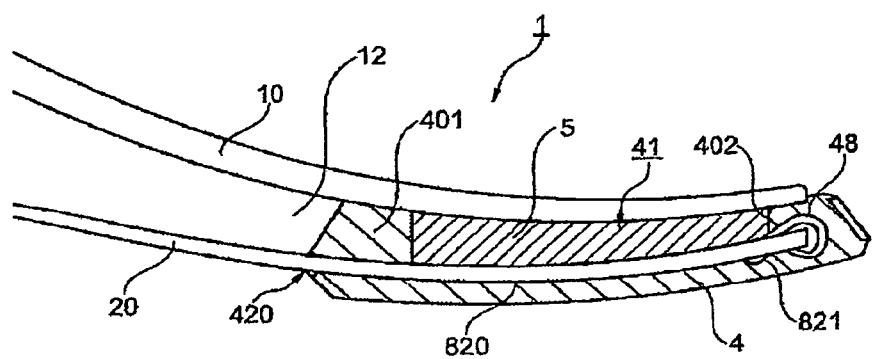
FIG. 3 shows a sectional view of part of an orthopedic component.

FIG. 3 shows a sectional illustration through a front part of a finished, assembled prosthetic foot as orthopedic component 1 with an upper first structural part 10 resting on the orienting device 4, said structural part 10 being in the form of a forefoot spring made of a fiber-reinforced plastics material, with the orienting device 4, and with the second structural part 20 inserted into the orienting device 4, said structural part being in the form of a base spring, which is likewise formed as a leaf spring made of a fiber-reinforced plastic material. The upper leaf spring rests on an upper support face, and the lower leaf spring rests on a lower support face 820. A channel 48 is formed at the front end (on the right-hand side in the illustrated exemplary embodiment) of the orienting device 4 and leads from the lower side of the second structural part 20 to the hollow space 41, which is enclosed by the second structural part 20, the first structural part 10, and the orienting device 4. Indentations 821 are formed in the support face 820, which is formed by the surface of the base of the orienting device 4 facing toward the second structural part 20, so that adhesive 5 completely filling the hollow space 41 can infiltrate the indentations 821 also below the second structural part 20 on account of a structured surface or the indentations 821, which are fluidically connected to the hollow space 41, such that at least the lower structural part 20 is surrounded by a number of sides or at a number of points by the adhesive 5. A feed connection 44 is advantageously arranged at the geodetically lowest point of the orienting device 4 during the assembly, for example on the lower side of the orienting device 4 in the case of the presented orientation, and is fluidically connected both to the indentations 821 and, on account of the channel 48, also to the hollow space 41. If adhesive 5 is now fed at the lowest point, said adhesive pushes through the structured surface on the upper side of the base of the orienting device 4 through the indentations 821, through the channel 48 into the hollow space 41, wherein the air previously enclosed therein is guided away through the outlet channel (not illustrated).

FIG. 3 additionally shows an insertion opening 420 for the second structural part 20, which opening in the illustrated exemplary embodiment is formed as a slot and ends at the height of the upper side of the base forming the support face 820. A first spacer 401 is arranged above the insertion opening 420, on which spacer the first structural part 20 is rested so that an intermediate space 12 is formed between the first structural part 10 and the second structural part 20, which intermediate space continues also toward the front, since a second spacer 402 is formed at the front end and serves as a support face for the first structural part 10. It can be seen from FIG. 3 that the insertion opening 420 is dimensioned so that the lower leaf spring can be pushed through and inserted in a tightly bearing manner. As the adhesive 5 is introduced, adhesive is thus prevented from being able to escape from a region of the insertion opening 420 around the second structural part 20. The sealing effect is increased by the pressing of the first structural part 10 against the spacer 401 and therefore against the second structural part 20. On account of the second press shoe 72, the support face 820 bears tightly against the structural part 20 so that no adhesive can escape as the hollow space 41 is filled.

The front end of the lower structural part 20 is received completely in the receiving device 4 and is protected and surrounded on all sides: the edging or framing of the upper support face for the first structural part protects the leaf springs at the periphery; the protection on the lower side is provided by the adhesive and the support face on the orienting device 4; merely the upper side is unprotected.

Figure 4:
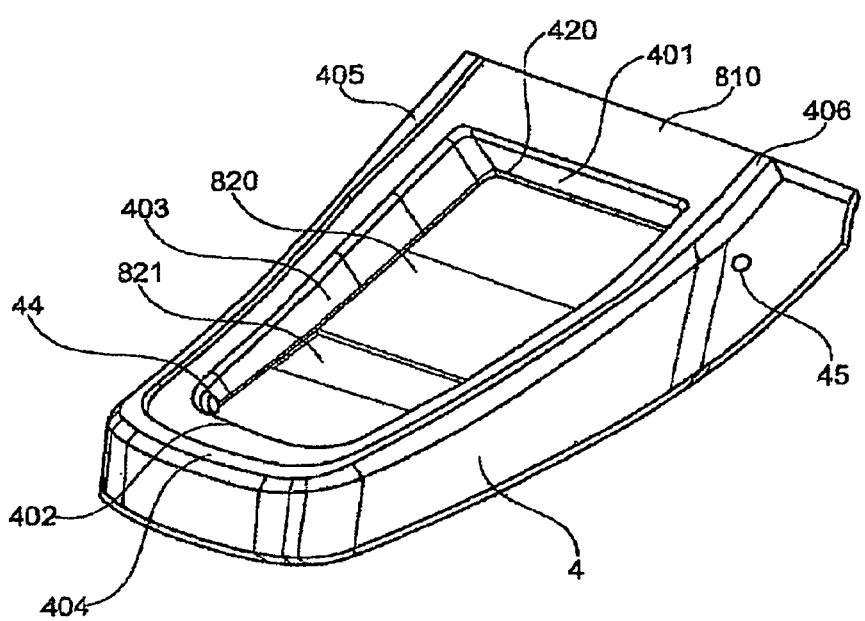
FIG. 4 shows a perspective view of an orienting device.

FIG. 4, in a perspective illustration, shows a receiving device 4 in accordance with the embodiment of the previous drawings. Besides the feed connection 44, the outlet channel 45, and the lower support face 820, the indentation 821 is illustrated slightly enlarged. The channel 48, which is fluidically connected to the indentation 821, is not illustrated. The spacers 401, 402 on the rear side and the front side can be seen. The spacers 401, 402 at the same time form, on their upper sides, an upper support face 810 for the first structural part (not illustrated), which is pressed by its lower side against the support face 810. The insertion slot or the insertion opening 420 ends at the height of the lower support face 820. A groove is made in the lateral spacers 403 laterally next to the support face 820, into which groove the leaf-shaped structural part 20 is inserted until it contacts the front termination of the orienting device 4.

The upper support face 810 is edged by side walls 404, 405, 406, which can correspond in terms of their material thickness to that of the upper structural part 10. Due to the side walls 404, 405, 406, a defined assignment of the upper structural part 10 to the orienting device 4 and therefore to the lower structural part 20 is ensured when the front and lateral edges of the structural part 10 bear against the respective side walls 404, 405, 406. If the height of the side walls 404, 405, 406 corresponds to the material thickness of the upper structural part 10, the surfaces can terminate in a flush manner.

Figure 5:
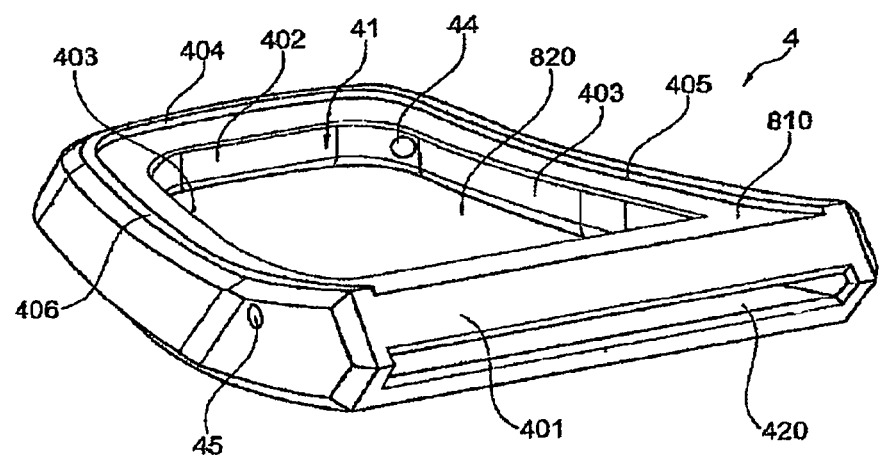
FIG. 5 shows another view of the orienting device from FIG. 4.

FIG. 5 shows the orienting device 4 in accordance with the previous embodiments in an oblique view from behind, from which the rear spacer 401, the front spacer 402, and the insertion opening 420 are very clearly visible. It can also be seen that the feed connection 44 is lower than the outlet channel 45, wherein both the feed connection 44 and the outlet channel 45 are formed within the spacer 403. A groove, in which the second structural part 20 can be inserted, is formed by an undercut in side walls formed below the spacer 403. The elevated side walls 404, 405, 406, which protrude past the upper support face 810, can also be seen, as can the support face 820 on the upper side of the base of the orienting device 4, which support face is flat in the illustrated exemplary embodiment. A receptacle is formed within the orienting device 4 by the side walls 402, 403 and the rear spacer 401, which receptacle can be completely filled with adhesive. By inserting the lower structural part 20 through the insertion opening 420, the insertion opening 420 is closed, so that the receptacle is only open upwardly after the insertion of the second structural part 20. If the structural part 10 (not illustrated) is rested on the upper support face 810, the hollow space 41 is closed. Once the hollow space 41 has been filled with the adhesive, this is connected in an adhesively bonded manner both to the orienting device 4 and to the two structural parts 10 and 20.

Figure 6:
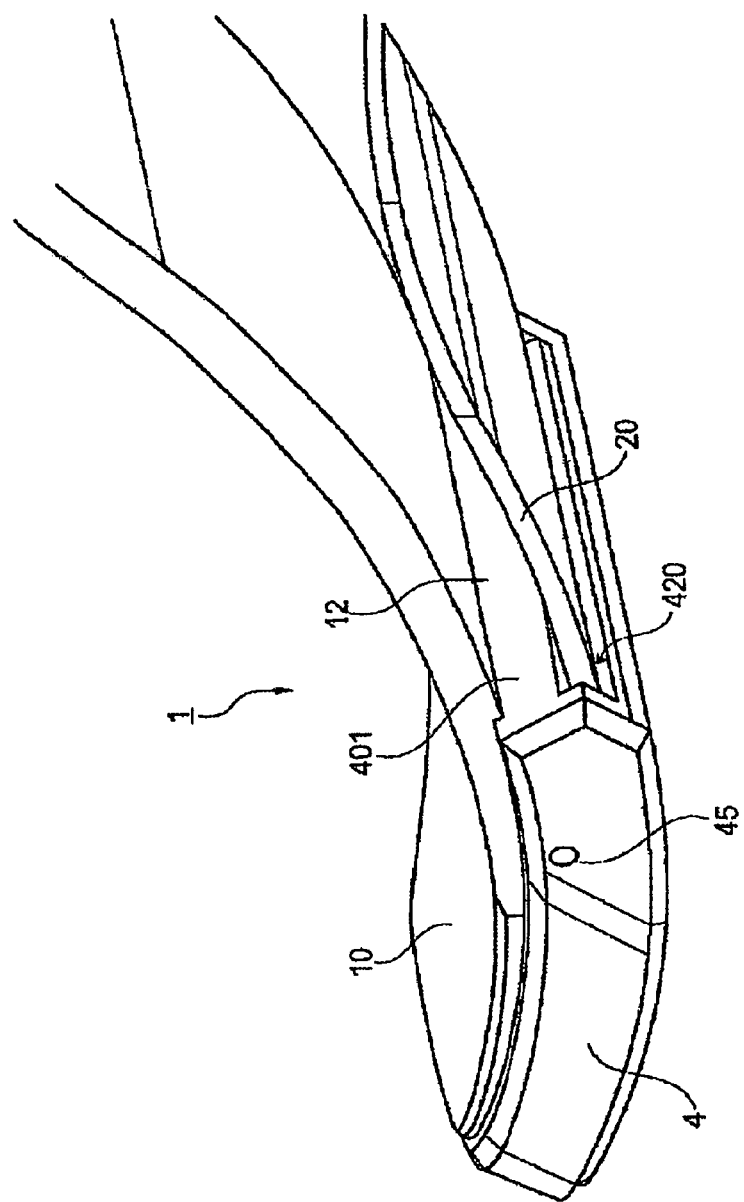
FIG. 6 shows a partial illustration of an orthopedic component obliquely from behind.

FIG. 6 shows a front part of the orthopedic component in the form of a prosthetic foot obliquely from behind in a finished, assembled state. The lower structural part 20 is inserted into the insertion opening 420, and the upper structural part 10 is rested and held on the support face 810 (not illustrated), with an intermediate space 12 thus being formed, this being ensured by the spacer 401. The outlet channel is arranged in a side wall, and the components 4, 10, 20 are permanently connected via the adhesive within the receiving device 4.

Figure 7:
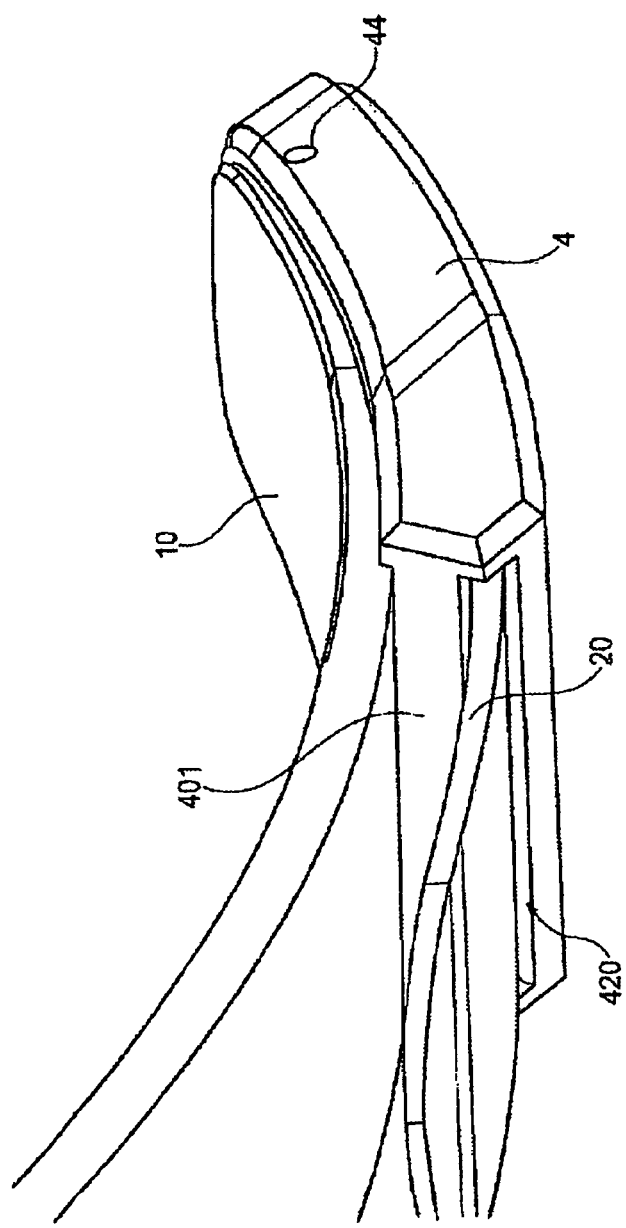
FIG. 7 shows a variant of FIG. 6.

FIG. 7 shows the embodiment according to FIG. 6 from the other side; the feed connection 44 is arranged on a front side wall of the orienting device 4.

Figure 8:
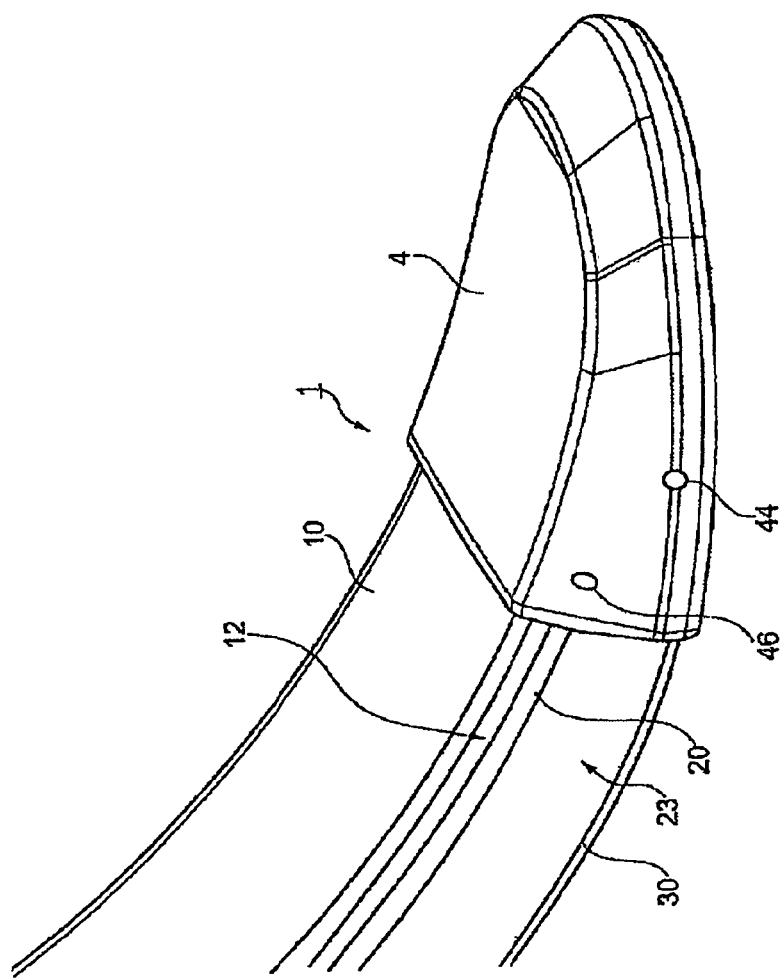
FIG. 8 shows a perspective partial illustration of a second embodiment.

FIG. 8 shows a variant of the invention in which, instead of just two structural parts, as is illustrated in FIGS. 1 to 7, three structural parts 10, 20, 30 are connected to one another via an orienting device 4. The orthopedic component 1 is again formed as a prosthetic foot and has a base spring as lower structural part 30. The forefoot spring is formed as a double leaf spring arrangement connected in parallel, comprising two leaf springs as middle structural part 20 and upper structural part 10. The orientation of the double spring and the base spring corresponds to the orientation as has been described further above, however different orientations and arrangements of the structural parts 10, 20, 30 in relation to one another are, in principle, possible and provided.

An intermediate spacer 23 is formed between the lower structural part 30 and the middle structural part 20, whereas a second intermediate spacer 12 is formed between the upper structural part 10 and the middle structural part 20. The intermediate space is formed by corresponding spacers within the orienting device 4.

The orienting device 4, in contrast to the previous embodiment, is closed upwardly, that is to say the upper structural part 10 is not rested on an upper support face in order to close off a hollow space, but rather all structural parts are inserted into the orienting device 4 from the rear side through insertion openings.

Since the spacing of the respective structural parts 10, 20, 30 continues within the orienting device 4, at least two hollow spaces are formed within the orienting device 4 and are separated from one another so that, in the illustrated exemplary embodiment, two feed connections 44, 46 are provided, such that the hollow spaces can be filled separately. It is thus possible to provide for example different adhesives, different adhesive temperatures, or other process features when required by the process.

Figure 9:
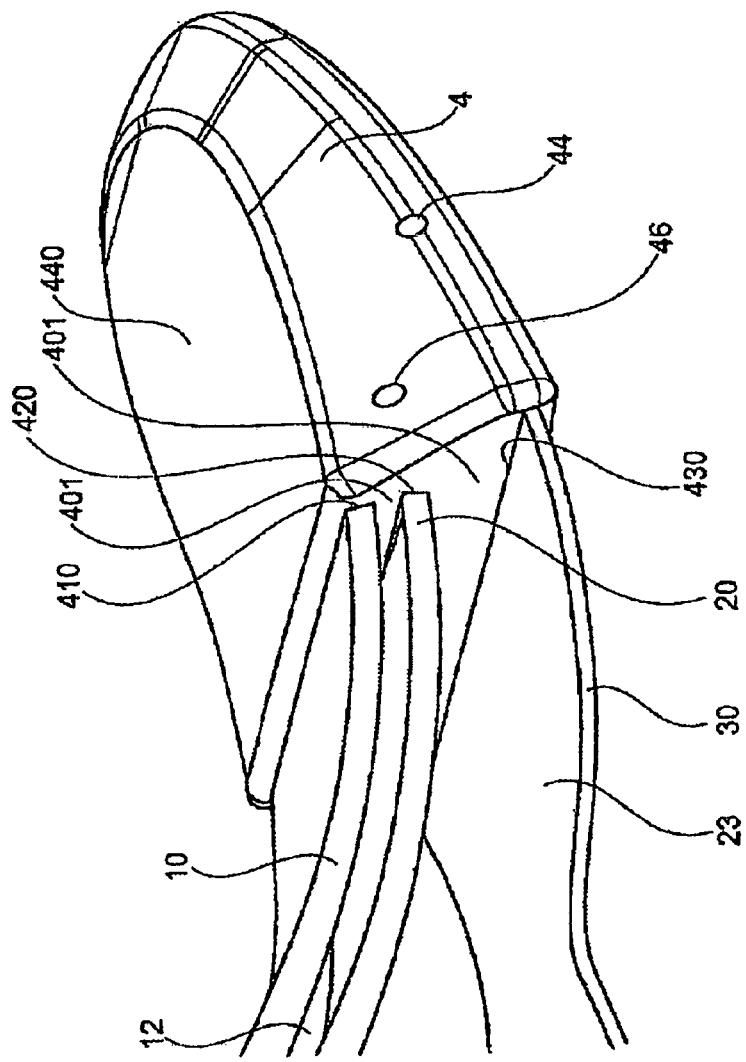
FIG. 9 shows another view of the embodiment from FIG. 8.

FIG. 9 shows the embodiment according to FIG. 8 in an oblique view from behind. The three insertion openings 410, 420, 430 on the rear end face of the orienting device 4 can be seen, as well as the two feed connections 44, 46 and the rear spacer 401 formed by the rear wall between the structural parts 10, 20, 30.

The insertion opening 430 for the lower structural part 30 is arranged, as in the previous embodiment, at the level of the lower support face 820, and the groove, preferably a peripheral groove in the side wall, and an optionally provided structuring of the support face can also be provided. Instead of the upwardly open design, a cover 440 is provided in the illustrated exemplary embodiment according to FIG. 9 so that the upper side of the upper structural part 10 is also covered by the material of the orienting device 4. The front ends of all structural parts 10, 20, 30 are thus surrounded completely by the orienting device 4 and are connected to one another and to the orienting device 4 via the adhesive.

Figure 10:
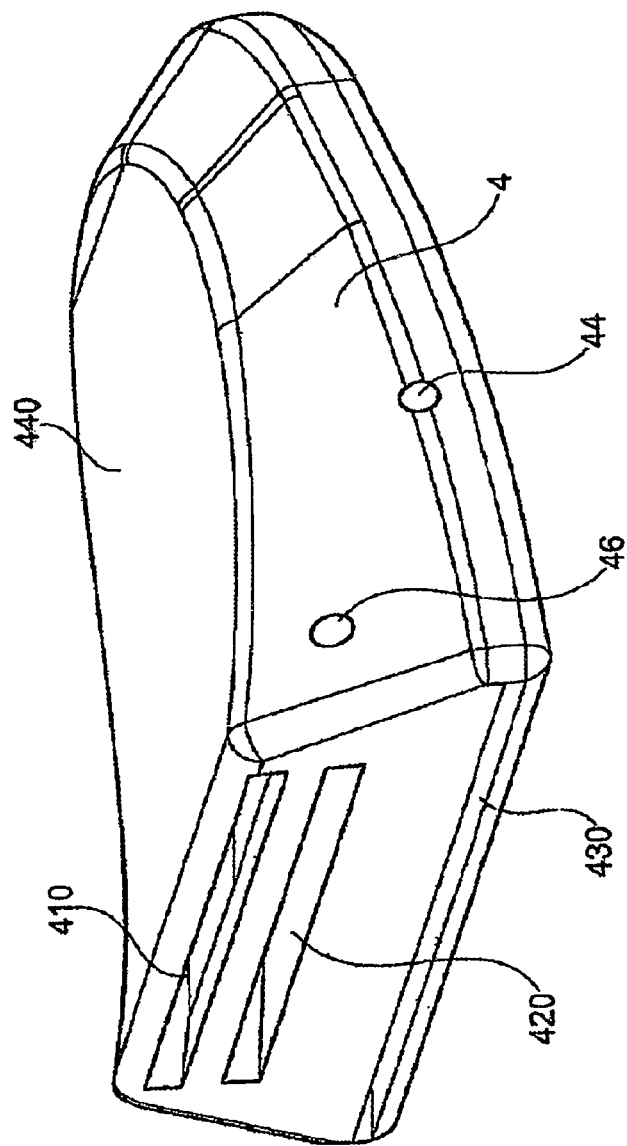
FIG. 10 shows an overall view of an orienting device of the second embodiment.

FIG. 10 shows the orienting device 4 in accordance with the second exemplary embodiment in an isolated illustration. The three insertion openings 410, 420, 430 on the rear side can be seen, as well as the two lateral feed connections 44, 46, which allow access to the intermediate spaces or hollow spaces within the orienting device 4 created by the insertion of the structural parts 10, 20, 30. The upper cover 440 forms the upper termination, and the base of the orienting device 4 forms the lower termination and a sort of sole in an embodiment of the orthopedic component as a prosthetic foot.

Figure 11:
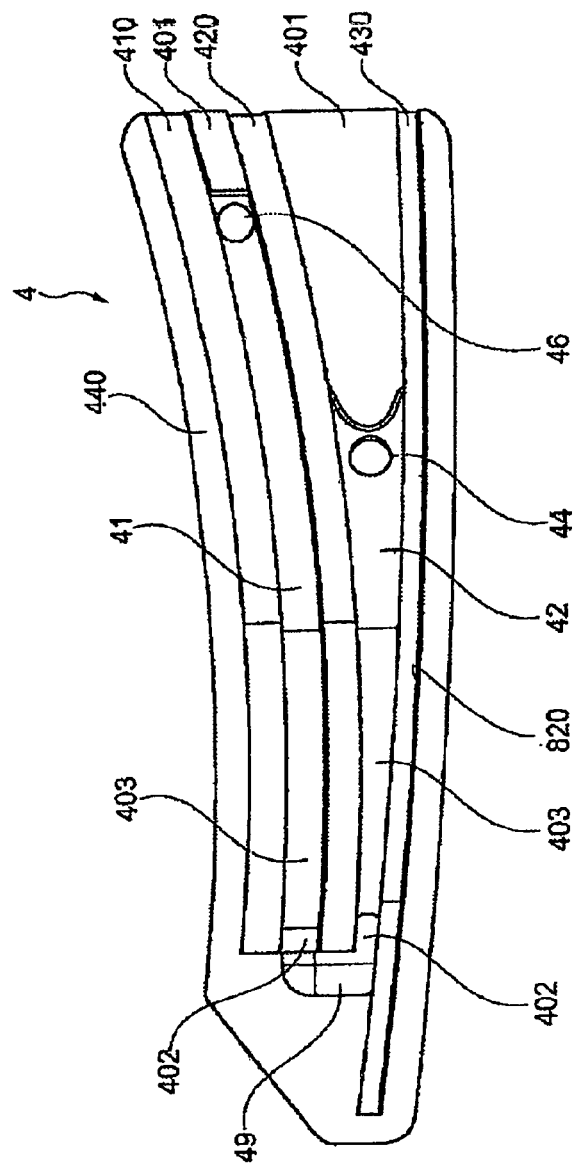
FIG. 11 shows a sectional illustration of FIG. 10.

FIG. 11 shows a sectional view of the orienting device 4, from which the insertion openings 410, 420, 430, the rear spacer 401, and the front and lateral spacers 402, 403 can be seen. A channel passing through the front spacer 402 is also formed so that adhesive can be admitted from the side through the feed connections 44, 46 into the hollow spaces 41, 42, which are formed by the orienting device 4 and the structural parts received therein. Alternatively to the embodiment illustrated in FIGS. 8 to 10, it is possible for just the lower opening 44 to be formed as a feed connection, whereas the upper opening is formed as an outlet channel, such that adhesive passes through the feed connection 44, through the hollow space 42 and the channel 49, into the hollow space 41 and then exits through the outlet channel. The support face 820 can be structured and can also be washed over or wetted by adhesive so that the middle structural part is surrounded both on the lower side and on the upper side by adhesive and is connected on both sides to a different structural part 10, 30. The closed cover 440 can also be seen, as can the closed front tip, and an insertion groove for the lower structural part, which protrudes beyond the channel 49 in the front direction. The feed connections 44, 46 or the feed connection 44 and the outlet channel are formed in the lateral spacers 403.

Figure 12:
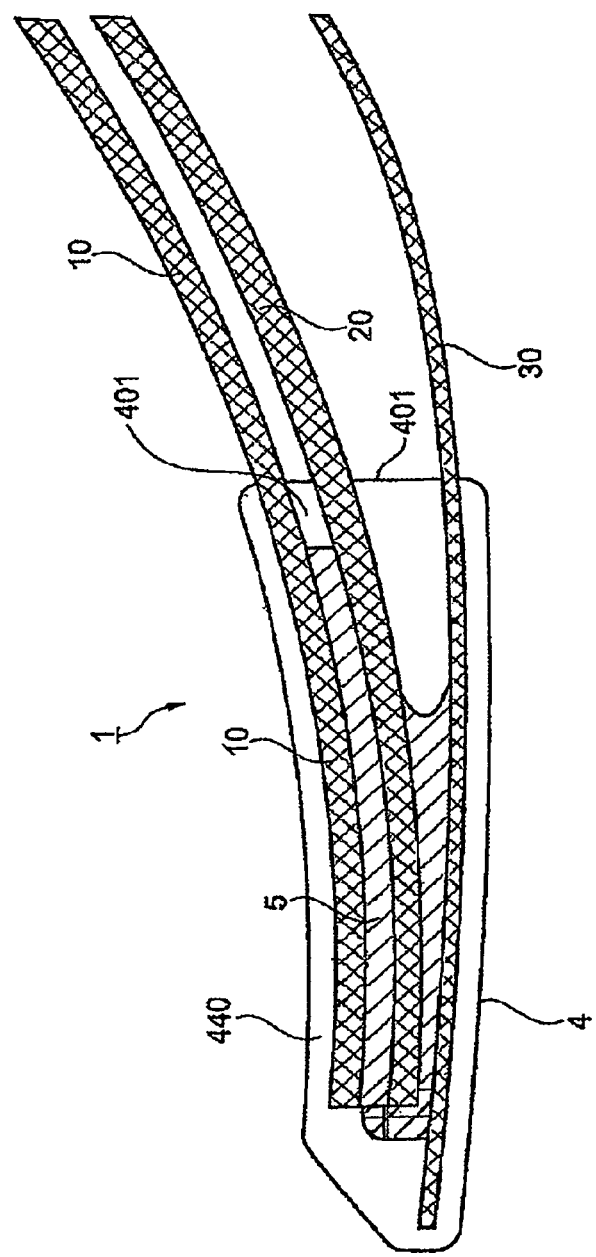
FIG. 12 shows a sectional illustration of FIG. 9.

FIG. 12 shows the front end of the orthopedic component 1 in the assembled state in a schematic sectional illustration. The three structural parts 10, 20, 30 in the form of leaf springs are inserted through the respective insertion openings into the orienting device 4, and the rear spacer 401, the spacer 403 (not illustrated) and the front spacer 402 are held at a distance from one another in the orienting device 4. The adhesive 5 has been introduced into the hollow space 41 through the feed connection 44 (not illustrated), has penetrated through the channel 49 into the upper hollow space 42, and has been guided away through the upper outlet channel 45 (not illustrated). No adhesive 5 has escaped rearwardly during manufacture through the sealed termination of the insertion openings 410, 420, 430 around the structural parts 10, 20, 30. The adhesive surrounds the second structural part 20 on the upper side, on the front side, and on the lower side.

Figure 13:
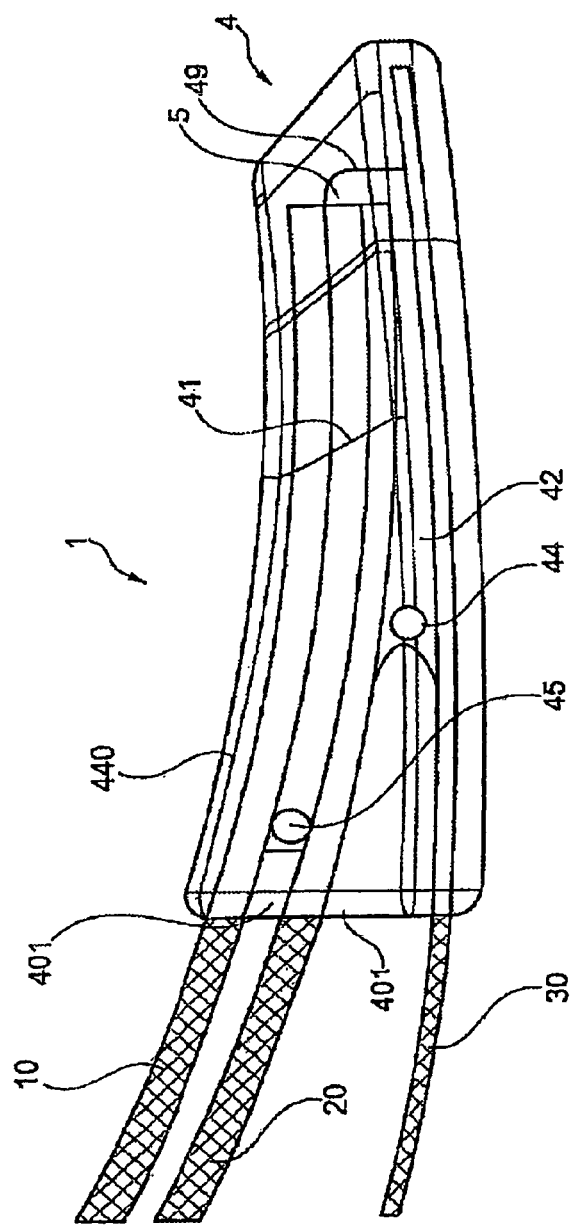
FIG. 13 shows another view of FIG. 12.

FIG. 13 shows a side view of the assembled prosthetic foot or the orthopedic component 1, in which case, instead of two feed connections, a lower feed connection 44 and an upper outlet channel 45 are provided in the orienting device 4. The three inserted structural parts 10, 20, 30 can also be seen, as can the rear spacer 401, the intermediate spaces or hollow spaces 41, 42, which are sealed to the rear by the inserted structural parts 10, 20, 30 and the upper cover 440, by means of which the upper leaf spring or the upper structural part 10 is also covered and protected completely by the orienting device 4.

The adhesive is pushed through the feed connection 44 into the lower hollow space 42, through the channel 49 into the upper hollow space 41, and out through the outlet channel 45; as soon as adhesive exits from the upwardly placed outlet channel 45, the feed of the adhesive through the feed connection 44 is stopped, the structural parts 10, 20, 30 are held in the desired assignment, and the adhesive is left to cure, such that all components 10, 20, 30, 4 are permanently connected to one another.

Figure 14:
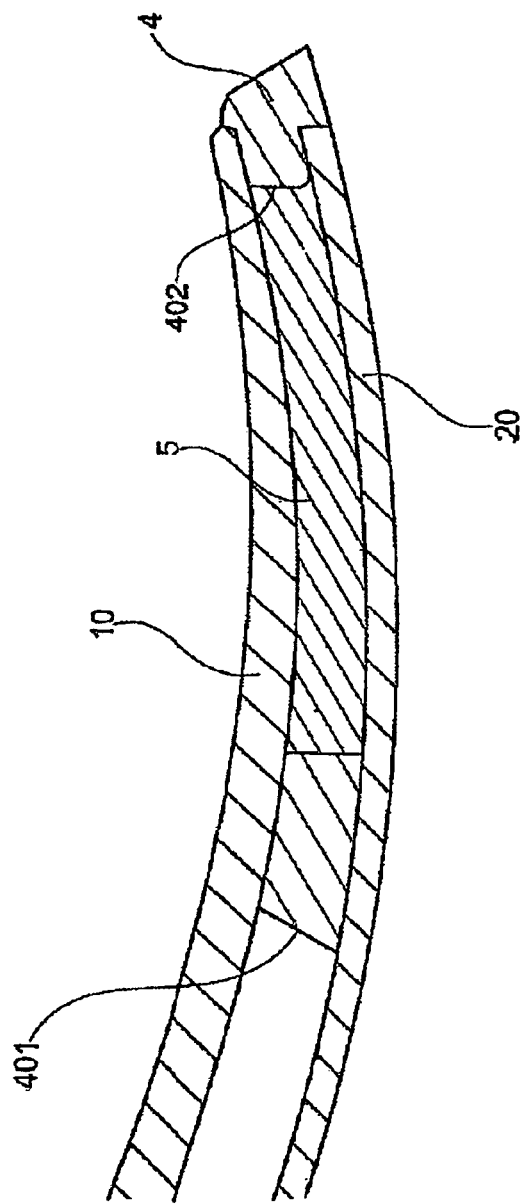
FIG. 14 shows a variant of the orienting device without base.

FIG. 14 shows a further variant of the invention in which the orienting device 4 is formed without a base on the lower side. The orienting device 4 is formed here as a frame with support faces for the structural parts 10, 20 placed above and below. The frame is peripheral with an enclosed opening, which is completed by the structural parts 10, 20 to form a hollow space, into which adhesive 5 is introduced, such that the lower side of the upper structural part 10 and the upper side of the lower structural part 20 are wetted with adhesive 5 opposite one another and are adhesively bonded to one another at the orienting device 4. Both structural parts 10, 20 are pressed against the relevant support face and are held pressed until the adhesive 5 has cured, the formed hollow space is sealed by pressing against the support faces, excess adhesive 5 exits only through the outlet channel arranged in a spacer, preferably via an outlet device, and therefore the component is not contaminated by adhesive 5.

Due to the method according to the invention and the orthopedic component according to the invention it is possible to adhesively bond two structural parts, in particular two fiber composite materials, using a liquid adhesive and at the same time to surround these structural parts in order to thus provide a protective casing. The orienting device fits on or to the components to be connected and forms a cavity therebetween which forms the receiving space for the liquid adhesive. In order to introduce the adhesive into the cavity or the hollow space and at the same time ventilate the cavity, relatively small openings in the form of feed channels or outlet channels are integrated into the orienting device or the mold and casing. Tube connectors can be inserted into these feed connections and outlet channels and can be connected to a feed tube and a venting tube. In order to ensure that the hollow space for the cavity is reliably sealed, the structural parts can be pressed together or can be pressed against the receiving device 4, wherein this can be made possible due to flexible materials. The material of the orienting device 4 is preferably a flexible, resilient material, such that a sealing abutment against the structural parts can be ensured by exerting pressure in the direction of the structural parts. Once the adhesive has been introduced and cured, the tube connectors are removed from the orienting device or the molding shell and the connection method is complete. The mold now no longer serves as a delimitation for the adhesive; it is used as a shell casing of the structural parts in order to protect the structural parts against damage and additionally in order to protect further parts, for example a casing or cosmetic product against damage by the structural parts connected to one another, which can have sharp edges.

Due to the device and the method it is possible to provide a mold for a liquid adhesive for the connection of two structural parts. The orientation of the components to be connected is ensured by the orienting device 4, and the component parts to be connected are also protected, the production method is clean, and there is no need for any post-processing of the joint area. The consumption of adhesive is limited, since no excess adhesive can escape, and a defined volume provided by the respective hollow spaces can serve as a basis for the calculation of the fed adhesive quantity. A quantity-controlled feed of adhesive is thus ensured, which on the one hand uses a minimal quantity of adhesive and on the other hand always provides sufficient adhesive in order to completely fill the hollow space.

The invention claimed is:

1. An orthopedic component, comprising:
   first and second structural parts; and
   an orienting device configured to orient the structural parts relative to each other,
   the orienting device comprising:
      a hollow space defined by interior surfaces of the orienting device; and
      an opening along a top surface of the orienting device, the opening being covered by the first structural part, the hollow space comprises a closed end and at least one insertion opening to receive the second structural part extending into the hollow space, the orienting device being adhesively bonded to the structural parts with adhesive received in the hollow space.

2. The orthopedic component of claim 1, wherein the interior surfaces of the orienting device that define the hollow space have a shape that corresponds to contoured surfaces of the structural parts.

3. The orthopedic component of claim 1, wherein the structural parts comprise leaf springs.

4. The orthopedic component claim of 1, wherein at least one of the structural parts is surrounded on a plurality of sides by the adhesive.

5. The orthopedic component claim of 1, wherein the orthopedic component is a prosthetic foot or an orthotic component.

6. The orthopedic component claim of 1, wherein the orienting device bears against or surrounds at least one of the structural parts on at least three sides.

7. The orthopedic component claim of 1, wherein the structural parts comprise fiber-reinforced plastic components.

8. The orthopedic component claim of 1, wherein the orienting device comprises a functional component.

9. The orthopedic component claim of 1, wherein the adhesive comprises a resilient material.

10. The orthopedic component claim of 1, wherein the orienting device includes spacers to space apart the structural parts from each other.

11. The orthopedic component claim of 1, wherein the adhesive completely fills the hollow space.

12. The orthopedic component of claim 1, wherein the closed end is a closed distal end, and at the least one insertion opening is at a proximal end to receive the second structural part.

\* \* \* \* \*